US010679751B2

(12) United States Patent
Im (10) Patent No.: US 10,679,751 B2
(45) Date of Patent: Jun. 9, 2020

(54) CELL ABNORMALITY DIAGNOSIS SYSTEM USING DNN LEARNING, AND DIAGNOSIS MANAGEMENT METHOD OF THE SAME

(71) Applicant: Wook-Bin Im, Seongnam-si (KR)

(72) Inventor: Wook-Bin Im, Seongnam-si (KR)

( * ) Notice: Subject to any disclaimer, the term of this patent is extended or adjusted under 35 U.S.C. 154(b) by 108 days.

(21) Appl. No.: 15/775,326

(22) PCT Filed: Oct. 11, 2016

(86) PCT No.: PCT/KR2016/011331
§ 371 (c)(1),
(2) Date: May 10, 2018

(87) PCT Pub. No.: WO2017/095014
PCT Pub. Date: Jun. 8, 2017

(65) Prior Publication Data
US 2018/0350467 A1  Dec. 6, 2018

(30) Foreign Application Priority Data

Nov. 30, 2015  (KR) .................. 10-2015-0168524

(51) Int. Cl.
*G16H 50/20* (2018.01)
*G06N 3/08* (2006.01)
(Continued)

(52) U.S. Cl.
CPC ......... *G16H 50/20* (2018.01); *G06K 9/00147* (2013.01); *G06N 3/08* (2013.01);
(Continued)

(58) Field of Classification Search
CPC .... G16H 50/20; G16H 40/20; G06K 9/00147; G06T 7/0012; G06N 3/10; G06N 3/08
See application file for complete search history.

(56) References Cited

U.S. PATENT DOCUMENTS 8,548,828 B1 * 10/2013 Longmire ............. G06Q 10/10
705/3
2012/0008838 A1 * 1/2012 Guyon .................. G06T 7/0012
382/128
(Continued)

FOREIGN PATENT DOCUMENTS

JP   05-054014 A   3/1993
JP   10-197522 A   7/1998
(Continued)

OTHER PUBLICATIONS

A Deep Neural Network-Based Method for Early Detection of Osteoarthritis Using Statistical Data Published Apr. 10, 2019 (Year: 2019).*
(Continued)

*Primary Examiner* — Nizar N Sivji
(74) *Attorney, Agent, or Firm* — John K. Park; Park Law Firm (57) ABSTRACT

The present invention is a technology relating to cell abnormality diagnosis system using DNN learning, which comprises a cell diagnosis device being installed in a each hospital and determining normal cells or dangerous cells on the basis of neural network as to inspection-subject cell photos; and a neural network learning server being connected to the Internet and performing DNN learning on the neural network of the cell diagnosis device. In particular, the present invention relates to a technology in which inspection-subject cell photos and diagnostic result data are acquired in each hospital and then uploaded to the neural network learning server, and then on the basis of this information the learning server performs DNN learning on a neural network model which is installed in the cell diagnosis device of the hospital so as to generate an upgrade neural network model as well as to download the same to the cell diagnosis device, so that cell diagnosis device becomes (Continued)

to form a neural network model which is optimized to the diagnosis environment of the hospital.

5 Claims, 9 Drawing Sheets

(51) Int. Cl.
    *G06K 9/00*     (2006.01)
    *G16H 40/20*     (2018.01)
    *G06N 3/10*     (2006.01)
    *G06T 7/00*     (2017.01)

(52) U.S. Cl.
    CPC .............. *G06N 3/10* (2013.01); *G06T 7/0012* (2013.01); *G16H 40/20* (2018.01)

(56) References Cited

U.S. PATENT DOCUMENTS

2016/0364857 A1* 12/2016 Reicher .................. G06F 19/00
2018/0293638 A1* 10/2018 Simpson .............. G01N 33/492

FOREIGN PATENT DOCUMENTS

| | | |
|---|---|---|
| JP | 3231810 B2 | 11/2001 |
| JP | 2002-090267 A | 3/2002 |
| JP | 2006-163517 A | 6/2006 |
| JP | 2012-026982 A | 2/2012 |
| KR | 10-2014-0042531 A | 4/2014 |
| WO | 2013089248 A1 | 4/2013 |

OTHER PUBLICATIONS

Deep Learning for Medical Image Processing: Overview, Challenges and Future Published 2017 (Year: 2017).*
Dermatologist-level classification of skin cancer with deep neural networks Published 2017 (Year: 2017).*
Keitaro Horikawa et all. Jubatus in Action: Report on Realtime Big Data Analysis by Jubatus, NTT Technical Review, NSDOCID XP 55596258, p. 1-8, vol. 10 No. 12 Dec. 2012.

* cited by examiner

CELL ABNORMALITY DIAGNOSIS SYSTEM USING DNN LEARNING, AND DIAGNOSIS MANAGEMENT METHOD OF THE SAME

FIELD OF THE INVENTION

The present invention is a technology relating to cell abnormality diagnosis system using DNN learning, which comprises a cell diagnosis device being installed in a each hospital and determining normal cells or dangerous cells on the basis of neural network as to inspection-subject cell photos; and a neural network learning server being connected to the Internet and performing DNN learning on the neural network of the cell diagnosis device.

In particular, the present invention relates to a technology in which inspection-subject cell photos and diagnostic result data are acquired in each hospital and then uploaded to the neural network learning server, and then on the basis of this information the learning server performs DNN learning on a neural network model which is installed in the cell diagnosis device of the hospital so as to generate an upgrade neural network model as well as to download the same to the cell diagnosis device. By the above constitution, the cell diagnosis device becomes to form a neural network model which is optimized to the diagnosis environment of the hospital.

BACKGROUND ART

It is conventionally used to inspect some desquamated cells which are taken from patients in order to diagnose disease. This includes taking samples of desquamated cells (i.e., inspection-subject cells) from patients, making slides by Papanicolaou stain and slide enclosure, and first examining these slides with optical microscopes by screeners (i.e., cytotechnologist). Those slides of abnormal finding in the first examination shall be under second examination so as to finalize the result of diagnosis on lesion.

However, it takes a very long time in the examination because screeners should manually and individually scan a lot of slides. Further, because the number of qualified screeners is very small, it is unlikely to promptly resolve the problem of taking long time in the first examination.

Further, because the examination is done under screeners' experience and skill, the accuracy of the first examination may be affected by screeners' personal condition. Conventionally, being concerned with this issue, more or less 10% are randomly selected out of slides of normal finding in the first examination in order to review the first examination. However, this is only a means of error monitoring or a means of putting pressure on the screeners, which cannot solve the cause of the problem structurally.

Therefore, if there is an electronic means that may provide consistent and reliable first diagnosis results for a large number of slides, it may be possible to get accurate final diagnosis results without relying solely on the skills of the screeners. Further, if screeners are supplemented or replaced by filtering out 70~80% of the large number of slides as no problem with inspecting the remaining 20~30% of slides, the time required for diagnosis may be shortened.

Further, with development of electronics industry and computer performance, electronic means have also been introduced in the medical field. However, individual hospitals are only introducing various technologies in their own tests yet, which renders diagnosis technology inconsistent and insufficiently reliable. Moreover, because each of large hospitals individually utilizes diagnostic result data of their own, technologies that improve the diagnostic accuracy of the electronic means are not well equipped.

Further, because this process is very complex and requires a high level of computing power, data is transmitted to a dedicated server at a remote location so that data processing is performed through a dedicated algorithm. Therefore, it takes a considerable time to obtain the diagnosis result. In addition, when the internet connection is obstructed, it becomes impossible to utilize it.

The applicant has referred the following documents with regard to the present invention.

(1) Korean Patent Application No. 10-2005-0039468, "Apparatus and method for cardiac diseases diagnoses based on ECG using neural network"

(2) Korean Patent Application No. 10-2002-0047898, "Face recognition method using artificial neural network, and the apparatus using thereof"

(3) Korean Patent Application No. 10-2009-0117305, "Pulse diagnosis robot system and pulse diagnosis method using the same"

(4) Korean Patent Application No. 10-2009-0117303, "Method and apparatus for providing fault diagnosis based on fNIRS for persons of developmental disorder"

DISCLOSURE OF INVENTION

Technical Problem

The present invention is proposed with referring to the mentioned above. It is, therefore, an object of the present invention to provide cell abnormality diagnosis system using DNN learning in which diagnosis accuracy of cell diagnosis devices in each hospital may be gradually improved with DNN learning which is intermittently performed by an Internet-connected external server without individually modifying each of neural network models.

It is another object of the present invention is to provide cell abnormality diagnosis system using DNN learning in which neural network models are constantly upgraded as specialized to the cell diagnosis device in each hospital.

Technical Solution

In order to achieve the object as above, the present invention provides a cell abnormality diagnosis system using DNN learning comprising a cell diagnosis device 100 for determining normal cells or dangerous cells on the basis of neural network as to inspection-subject cell photos and a neural network learning server 200 being connected to the cell diagnosis device 100 via Internet for performing DNN learning on the neural network, which comprising: a cell diagnosis device 100 including: neural network modeler 110 of storing low-rank neural network model which is pre-learned so as to differentiate normal cells from dangerous cells, cell image processor 120 of providing inspection-subject cell photos from outside into the low-rank neural network model in pixel basis, cell abnormality diagnoser 130 of detecting abnormality out of the inspection-subject cell photos which is provided by the cell image processor, and NN model updater 140 of upgrading the low-rank neural network model by downloading high-rank neural network model from the neural network learning server 200 via Internet; and a neural network learning server 200 including: lesion database 210 of storing pluralities of normal cell photos and lesion cell photos which are pre-classified by each kind of lesions, NN model generator 220 of generating high-rank neural network model on the basis of the normal or dangerous pre-classified data in the lesion database, DNN learning processor 230 of performing DNN learning for the high-rank neural network model on the basis of the normal or dangerous pre-classified data in the lesion database, and learning model provider 240 of providing the high-rank neural network model to the NN model updater by downloading.

In the present invention, the cell diagnosis device 100 may further comprise: diagnosis data provider 150 of uploading to the neural network learning server 200 the inspection-subject cell photos and diagnostic result data which are obtained by actual diagnosis result for patients, and NN model cumulative updater 160 of downloading the upgrade neural network model being DNN learned from the neural network learning server 200 so as to substitute the low-rank neural network model with the downloaded upgrade neural network model. And, the neural network learning server 200 may further comprise: cumulative learning model generator 250 of being uploaded with the inspection-subject cell photos and the diagnostic result data by the cell diagnosis device and then of performing DNN learning on the low-rank neural network model of the cell diagnosis device on the basis of the uploaded so as to generate an upgrade neural network model for the cell diagnosis device, and cumulative learning model provider 260 of providing the upgrade neural network model to the cell diagnosis device by downloading.

In the present invention, the cell diagnosis device 100 may further comprise: low-rank model provider 170 of uploading its own low-rank neural network model to the neural network learning server 200 for DNN learning. And, the cumulative learning model generator 250 of the neural network learning server 200 may perform DNN learning on the low-rank neural network model which is provided by the low-rank model provider of the cell diagnosis device.

In the present invention, the neural network learning server 200 may further comprise: low-rank model identifier 270 of managing the recently downloaded neural network model for each of the cell diagnosis devices so as to identify the low-rank neural network model of the cell diagnosis device which has uploaded the inspection-subject cell photos and the diagnostic result data and so as to provide the identified low-rank neural network model to the cumulative learning model generator 250.

Further, the present invention provides a diagnosis management method of cell abnormality using DNN learning in a cell abnormality diagnosis system including a cell diagnosis device 100 for determining normal cells or dangerous cells on the basis of neural network as to inspection-subject cell photos and a neural network learning server 200 being connected to the cell diagnosis device 100 via Internet for performing DNN learning on the neural network, which comprising: (a) for the cell diagnosis device of storing low-rank neural network model which is pre-learned so as to differentiate normal cells from dangerous cells; (b) for the cell diagnosis device of providing inspection-subject cell photos from outside into the low-rank neural network model in pixel basis; (c) for the cell diagnosis device of detecting abnormality out of the inspection-subject cell photos; (d) for the neural network learning server of storing pluralities of normal cell photos and lesion cell photos which are pre-classified; (e) for the neural network learning server of generating high-rank neural network model on which DNN learning is performed on the basis of the pre-classified data of pluralities of normal cell photos and lesion cell photos; (f) for the neural network learning server of providing the high-rank neural network model to the cell diagnosis device by downloading; (g) for the cell diagnosis device of downloading the high-rank neural network model from the neural network learning server via Internet and then of upgrading the low-rank neural network model.

Preferably, the present invention may further comprise: (h) for the cell diagnosis device of obtaining inspection-subject cell photos and diagnostic result data by actual diagnosis result for patients and then of uploading the same to the neural network learning server 200; (i) for the neural network learning server of performing DNN learning on the basis of the inspection-subject cell photos and diagnostic result data which has received from the cell diagnosis device so as to generate an upgrade neural network model; (j) for the neural network learning server of providing the upgrade neural network model to the cell diagnosis device by downloading; and (k) for the cell diagnosis device of downloading the upgrade neural network model from the neural network learning server and then of upgrading the low-rank neural network model.

Further, the non-transitory computer-readable medium according to the present invention contains program code which executes the above-mentioned diagnosis management method of cell abnormality using DNN learning.

Advantageous Effects

According to the present invention, it is advantageous in that cell diagnosis devices in each hospital may quickly produce diagnosis result by carrying out diagnosis process by itself with internally-installed neural network model, and further in that they may robustly carry out diagnosis process even when Internet connection is unstable.

Further, according to the present invention, it is also advantageous in that, without individually modifying each of neural network models, by upgrading low-rank neural network model of the cell diagnosis device with high-rank neural network model which is downloaded from a dedicated external neural network learning server, the diagnosis accuracy of cell diagnosis devices in each hospital may be gradually improved.

Further, according to the present invention, it is also advantageous in that, because the neural network learning server performs DNN learning on neural network model for a hospital on the basis of inspection-subject cell photos and diagnostic result data which have been acquired from the same hospital, a cell diagnosis device may have neural network model which is gradually upgraded as optimized to the diagnosis environment of each hospital, e.g., race, gender, ages, harmful environment around, disease inducers, and common disease in each area so as to eventually improve the accuracy of diagnosis.

EMBODIMENT FOR CARRYING OUT THE INVENTION

The invention shall be described below in detail with reference to the accompanying drawings.

Figure 1:
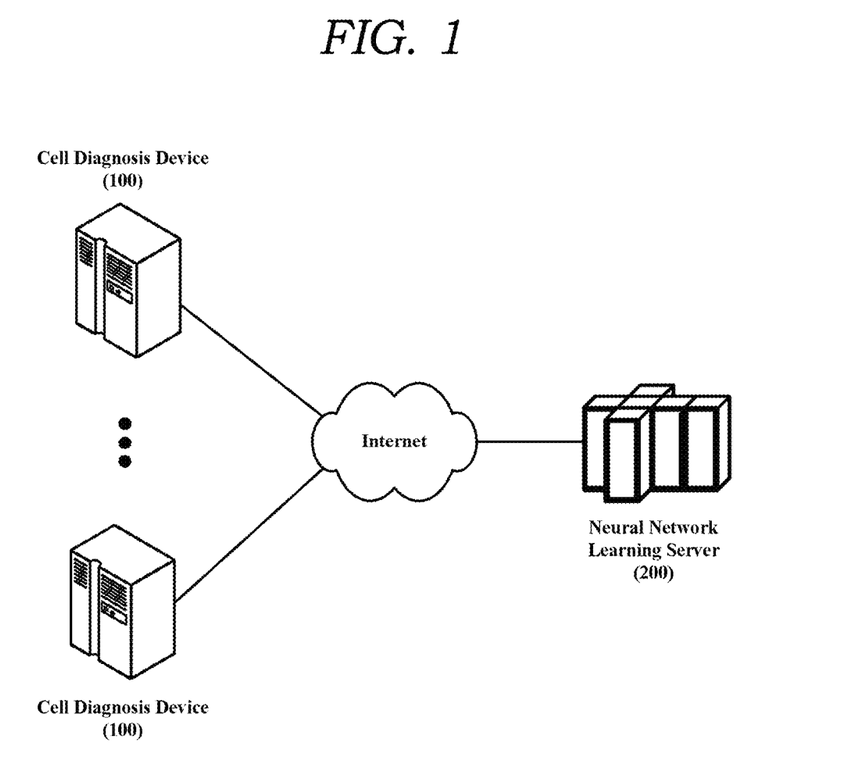
FIG. 1 is an exemplary view roughly illustrating the cell abnormality diagnosis system using DNN learning according to the present invention.

FIG. 1 is an exemplary view roughly illustrating the cell abnormality diagnosis system using DNN learning according to the present invention. Referring to FIG. 1, in the present invention a neural network learning server 200 is connected to at least one cell diagnosis devices 100 via Internet.

First, the cell diagnosis device 100 is a device for determining cell abnormality and is equipped with neural network model which is preferably implemented as computer software or computer hardware.

In this specification, the neural network model which is installed in a cell diagnosis device 100 is called as 'low-rank neural network model' for ease of description. The cell diagnosis device 100 is provided with inspection-subject cell photos, and then provides the same into the low-rank neural network model. Further, corresponding to the computation result in the low-rank neural network model, the cell diagnosis device 100 determines normal cells or dangerous cells. In this specification, 'a normal cell' represents one of sparse possibility of lesion, whereas 'a dangerous cell' represents one of non-ignorable possibility of lesion and of requiring further examination.

The neural network learning server 200 performs deep learning of DNN learning technique on neural network model of the cell diagnosis device 100 so as to generate high-rank neural network model, and then provide the high-rank neural network model to the cell diagnosis device 100 by downloading via Internet. In this specification, the neural network model which is generated by the neural network learning server 200 is called as 'high-rank neural network model' for ease of description. By DNN learning of the neural network learning server 200, the cell diagnosis device 100 becomes to constantly upgrade its own neural network model.

By the way, the cell diagnosis devices 100 are devices for diagnosing patients, which are installed in hospitals which are preferably located far away from the neural network learning server 200. A plurality of cell diagnosis devices 100 may be utilized for one neural network learning server 200.

By the way, because the cell diagnosis device 100 carries out diagnosis on inspection-subject cell photos by itself on the basis of neural network model which has downloaded from the neural network learning server 200, the cell diagnosis device 100 may promptly produce the diagnosis result even though being based on neural network technology and further may robustly carry out diagnosis process even when Internet is offline.

Further, the terms in this specification, i.e., neural network model, low-rank neural network model, and high-rank neural network model are selected so as to represent that the neural network learning server 200 performs "DNN (Deep Neural Network) learning" of supervised learning approach by use of a lot of pre-categorized normal cell photos and lesion cell photos.

Figure 2:
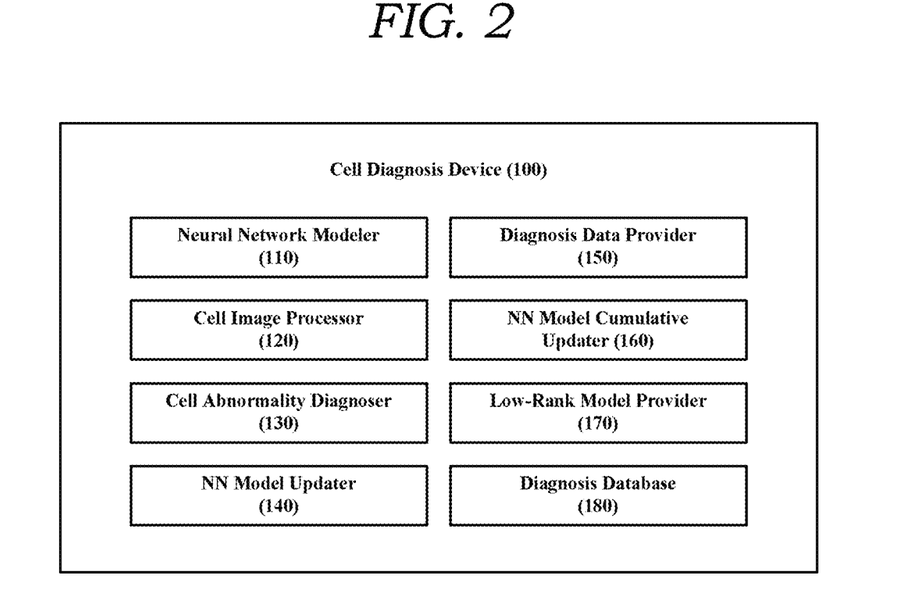
FIG. 2 is a block diagram of the cell diagnosis device according to the present invention.

FIG. 2 is a block diagram of the cell diagnosis device according to the present invention. Referring to FIG. 2, the cell diagnosis device 100 of the cell abnormality diagnosis system of the present invention may comprise neural network modeler 110, cell image processor 120, cell abnormality diagnoser 130, NN model updater 140, diagnosis data provider 150, NN model cumulative updater 160, low-rank model provider 170, and diagnosis database 180.

Firstly, the neural network modeler 110 stores low-rank neural network model which is pre-learned so as to differentiate normal cells from dangerous cells as to the inspection-subject cell photos. Preferably, the neural network modeler 110 may be configured in manufacturing process or may be downloaded from the neural network learning server 200. Further, the neural network modeler 110 is preferably a dedicated program which has lesion cell detecting algorithm for inspecting whether desquamated cells taken from patients are lesion cells or not.

Preferably, lesion cell detecting algorithm for the low-rank neural network model may comprise pattern recognition algorithm and lesion feature searching algorithm. The pattern recognition algorithm is an algorithm for recognizing patterns of cells out of the inspection-subject cell photos. Further, the lesion feature searching algorithm is an algorithm for searching the patterns of inspection-subject cells for any of features of lesions, e.g., by overlapping, which are generally appears in lesion cells for each kind of lesions.

The cell image processor 120 provides the inspection-subject cell photos into the low-rank neural network model in pixel basis, in which the inspection-subject cell photos are also provided from outside. The procedure of taking inspection-subject cells from patients and obtaining the inspection-subject cell photos may be carried out as a workflow.

The cell abnormality diagnoser 130 detects abnormality out of the inspection-subject cell photos on the basis of the result of computation by the neural network modeler 110 on the inspection-subject cell photos which is provided by the cell image processor 120. The abnormality relates to dangerous cells which have substantial possibility of lesion cells.

The neural network (NN) model updater 140 downloads a high-rank neural network model from the neural network learning server 200 via Internet and then upgrades the low-rank neural network model of the neural network modeler 110 by use of the downloaded high-rank neural network model. For example, the downloaded high-rank neural network model may replace the low-rank neural network model of the neural network modeler 110.

The diagnosis data provider 150 uploads to the neural network learning server 200 the inspection-subject cell photos and diagnostic result data which are obtained by actual diagnosis result for patients in each hospital. This aims for learning its own neural network model (i.e., the low-rank neural network model) being optimized to the diagnosis environment of the hospital.

The neural network (NN) model cumulative updater 160 downloads the upgrade neural network model from the neural network learning server 200 in which the upgrade neural network model has been cumulatively learned with reflecting the inspection-subject cell photos and the diagnostic result data which are obtained in each hospital so as to upgrade the low-rank neural network model. In the present invention, the neural network learning server 200 performs the cumulative learning process for neural network model by DNN learning technology.

The low-rank model provider 170 uploads the low-rank neural network model which the neural network modeler 110 currently owns to the neural network learning server 200 so that the neural network learning server 200 may perform DNN learning on the low-rank neural network model being optimized to the inspection-subject cell photos and the diagnostic result data.

The diagnosis database 180 collects and stores inspection-subject cell photos and diagnostic result data by actual diagnosis of patients for each hospital. The diagnosis data provider 150 shall upload these stored inspection-subject cell photos and diagnostic result data to the neural network learning server 200 at an appropriate timing (e.g., last Sunday of every month at 10 am) so as to be utilized in DNN learning of neural network model.

In another embodiment, while diagnosis management system (not shown) being equipped with hospital information system, the diagnosis data provider 150 of the cell diagnosis device 100 may be configured to access the hospital information system so as to upload inspection-subject cell photos and diagnostic result data in the diagnosis management system to the neural network learning server 200.

Figure 3:
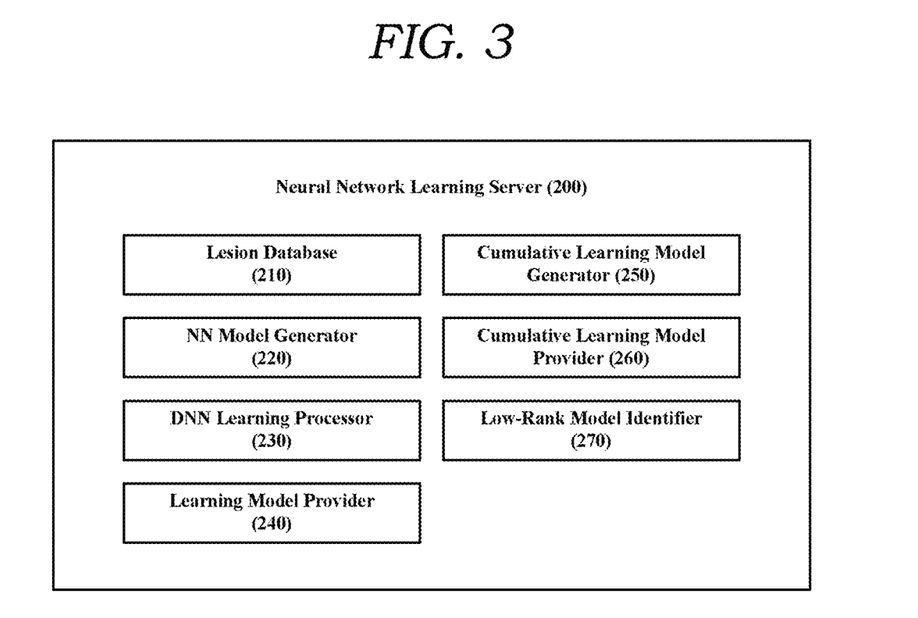
FIG. 3 is a block diagram of the neural network learning server according to the present invention.

FIG. 3 is a block diagram of the neural network learning server according to the present invention. Referring to FIG. 3, the neural network learning server 200 of the cell abnormality diagnosis system of the present invention may comprise lesion database 210, NN model generator 220, DNN learning processor 230, learning model provider 240, cumulative learning model generator 250, cumulative learning model provider 260, and low-rank model identifier 270.

Firstly, the lesion database 210 stores sufficiently many pluralities of normal cell photos and lesion cell photos which are pre-classified by each kind of lesions. In the present invention, it is preferable to constantly update the normal cell photos and the lesion cell photos. The update may be performed by use of the data which is uploaded by the cell diagnosis device 100 or by use of any data which is provided by other channels, e.g., data CDs.

The neural network (NN) model generator 220 constantly generates high-rank neural network model on the basis of the pre-classified data, i.e., the data being pre-classified as normal cell photos or lesion cell photos, in the lesion database. It is preferable that the high-rank neural network model which the NN model generator 220 generates is constantly upgraded by DNN learning which is performed by the DNN learning processor 230.

The Deep Neural Network (DNN) learning processor 230 performs DNN learning for the high-rank neural network model on the basis of the pluralities of data, the normal or dangerous pre-classified data, which are provided by the lesion database 210.

The learning model provider 240 provides the high-rank neural network model to the cell diagnosis device 100, i.e., specifically to the NN model updater 140 by downloading via Internet, in which the high-rank neural network model is upgraded by the DNN learning processor 230 through DNN learning.

The cumulative learning model generator 250 is uploaded with the inspection-subject cell photos and the diagnostic result data by a specific cell diagnosis device and then performs DNN learning on the low-rank neural network model of the cell diagnosis device on the basis of the uploaded. By this process, the cumulative learning model generator 250 generates an upgrade neural network model which is specialized to the cell diagnosis device having provided the inspection-subject cell photos and the diagnostic result data.

By the way, the cumulative learning model generator 250 shall identify the low-rank neural network model of the cell diagnosis device 100. If the low-rank model provider 170 provides the low-rank neural network model of the cell diagnosis device 100, the cumulative learning model generator 250 may use of the information. Alternatively, the low-rank model identifier 270 may manage the recently downloaded neural network model for each of the cell diagnosis devices 100, as shall be described below.

The cumulative learning model provider 260 provides the upgrade neural network model which is generated by the cumulative learning model generator 250 to the cell diagnosis device 100 by downloading via Internet.

The low-rank model identifier 270 manages the recently downloaded neural network model for each of the cell diagnosis devices 100 so as to identify the low-rank neural network model of the cell diagnosis device 100 which has uploaded the inspection-subject cell photos and the diagnostic result data and so as to provide the identified low-rank neural network model to the cumulative learning model generator 250.

Figure 4:
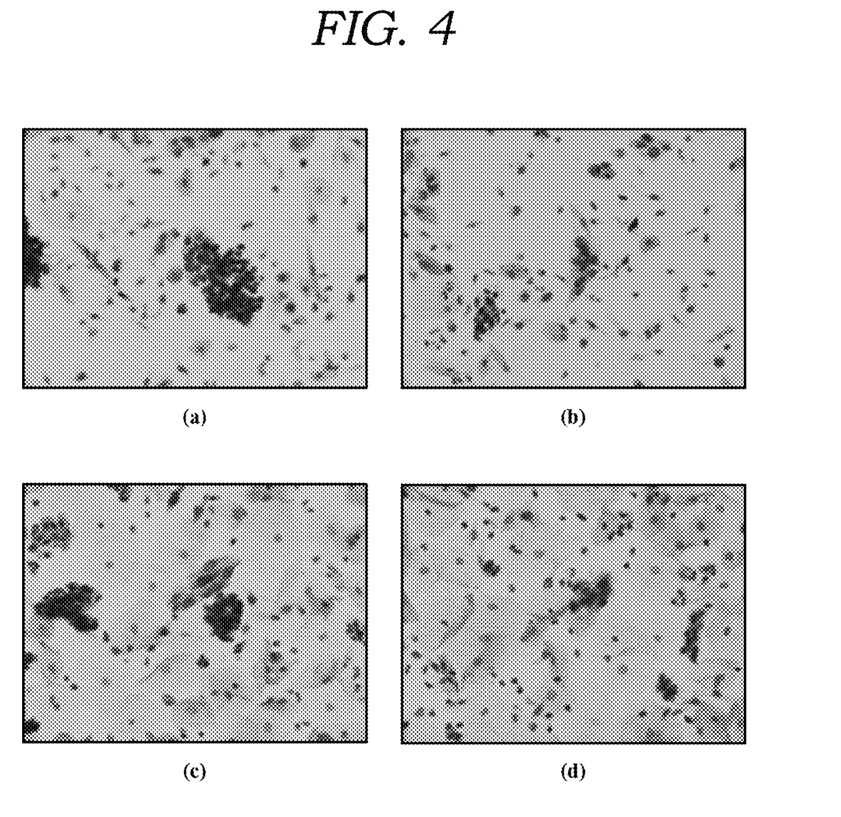
FIG. 4 shows an example of inspection-subject cell photos according to the present invention.
Figure 5:
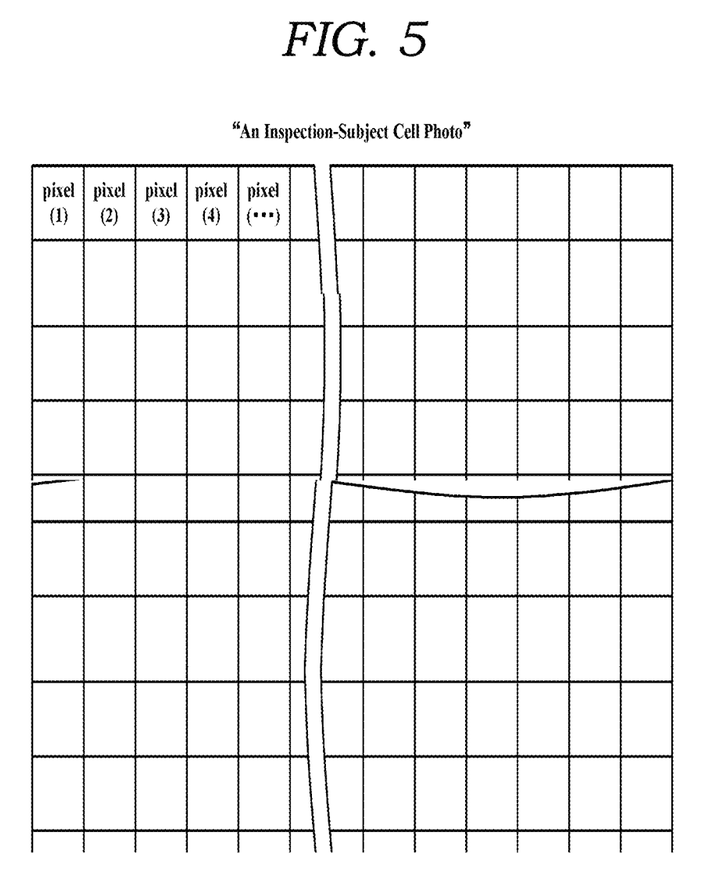
FIG. 5 is an exemplary view illustrating an inspection-subject cell photos in pixels according to the present invention.
Figure 6:
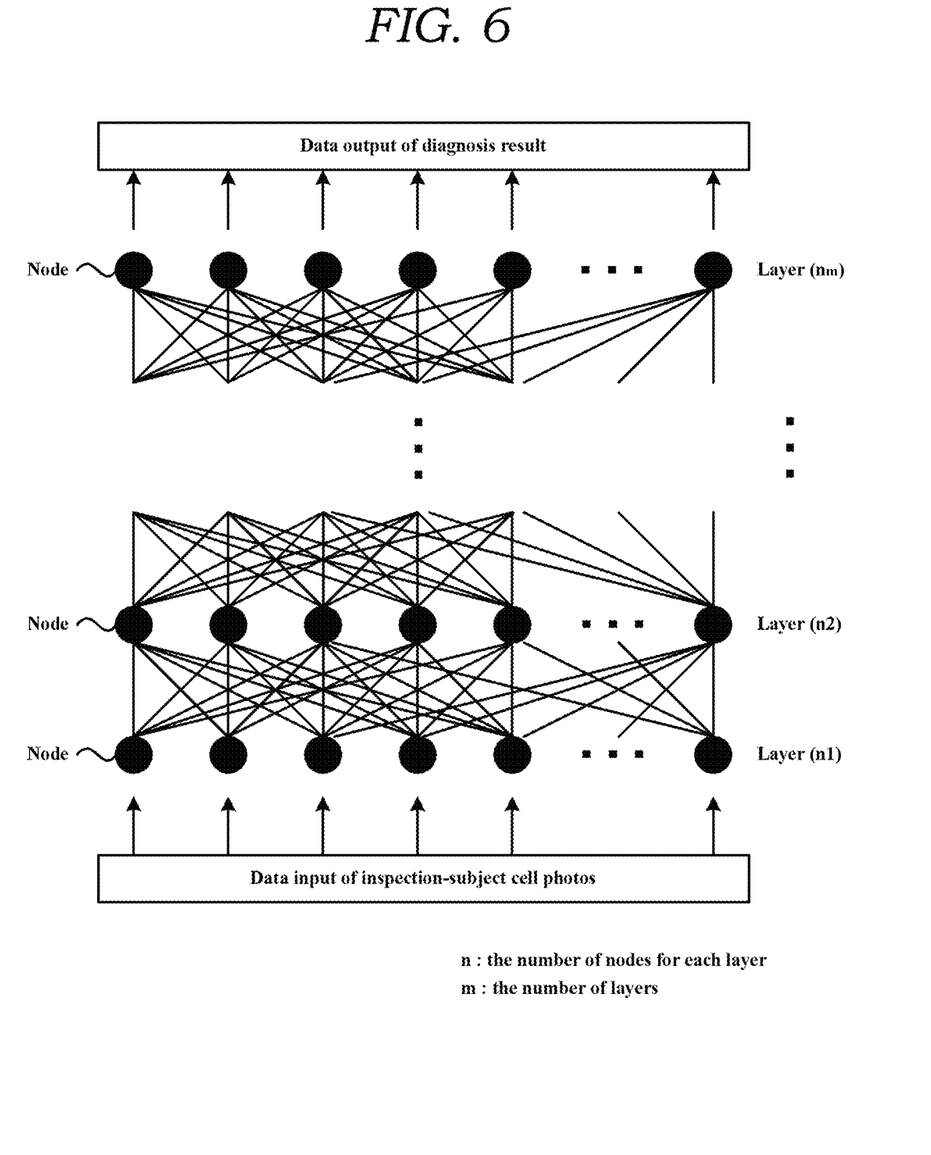
FIG. 6 is an exemplary view illustrating a procedure of inspecting whether there is abnormality out of the inspection-subject cell photos by providing data of the same into neural network model.

FIG. 4 shows an example of inspection-subject cell photos which are taken according to the present invention. FIG. 5 is an exemplary view illustrating an inspection-subject cell photos in pixels according to the present invention. FIG. 6 is an exemplary view illustrating a procedure of inspecting whether there is abnormality out of the inspection-subject cell photos by providing data of the same into neural network model.

First, FIG. 4 shows an example of four (4) inspection-subject cell photos which are supplied as workflow. Meanwhile, the number of inspection-subject cell photos is not limited to four (4) in the present invention. For ease of description, an inspection-subject cell photo out of FIGS. 4 (*a*) to (*d*) is shown in FIG. 5 in pixel basis.

Referring to FIG. 5, the cell image processor 120 of the cell diagnosis device 100 provides inspection-subject cell photos for a series of cell inspections into an algorithm of low-rank neural network model in pixel basis.

Referring to FIG. 6, the inspection-subject cell photos are provided to the low-rank neural network model of the cell diagnosis device 100, and then the low-rank neural network model outputs diagnostic result data through a series of computations in each node. By the way, because operation theory of neural network has already been generally proposed in the prior art and further the present invention does not claim to the neural network technology itself, the detailed description thereof shall be omitted herein.

Further, on the basis of the diagnostic result data which is outputted by the low-rank neural network model, the cell abnormality diagnoser 130 of the cell diagnosis device 100 detects whether the inspection-subject cell photos are normal cells or dangerous cells. The detection of dangerous cells represents that in-depth examination is further required.

Figure 7:
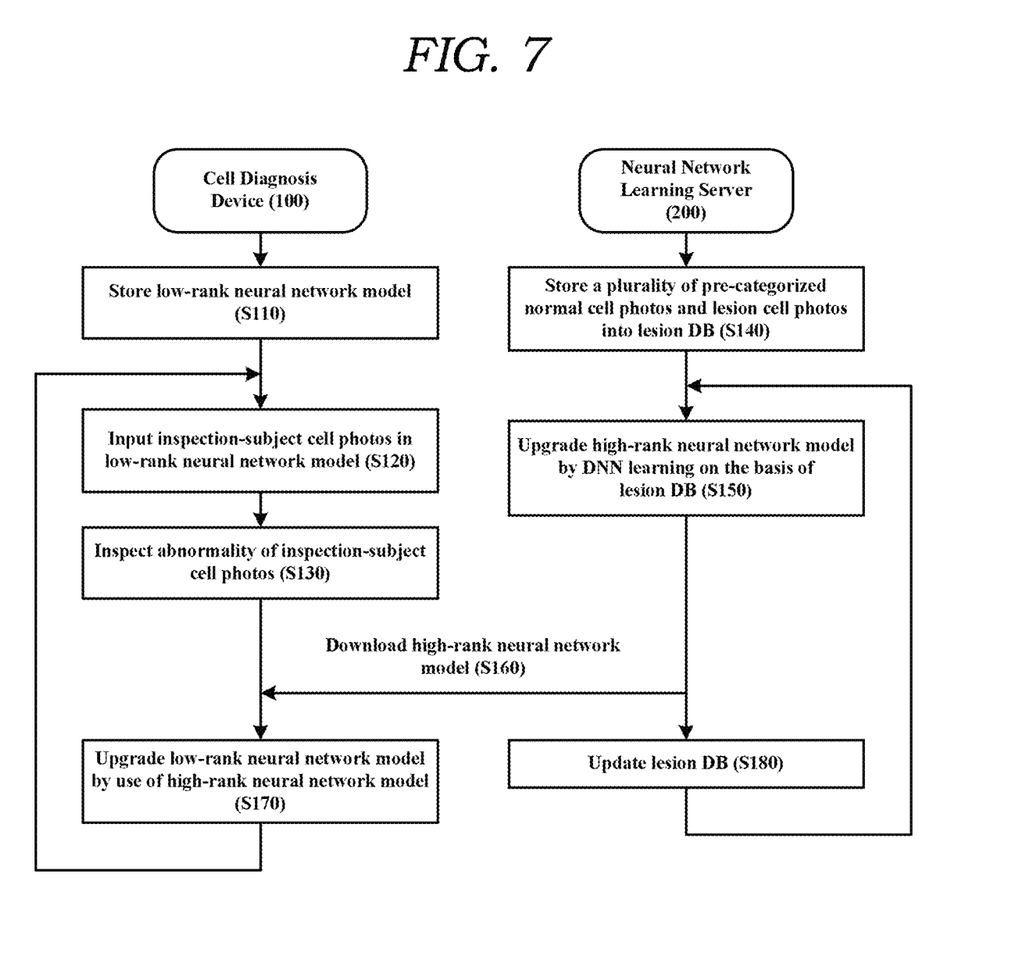
FIG. 7 is a flowchart illustrating an embodiment of cell abnormality diagnosis procedure using DNN learning according to the present invention.

FIG. 7 is a flowchart illustrating an embodiment of cell abnormality diagnosis procedure using DNN learning according to the present invention.

Step (S110): The present invention relates to a technology for inspecting cell abnormality by utilizing a cell diagnosis device 100 for determining normal cells or dangerous cells on the basis of neural network as to inspection-subject cell photos and a neural network learning server 200 being connected to the inspecting device via Internet for performing DNN learning on the neural network.

In order to achieve the object, the neural network modeler 110 of the cell diagnosis device 100 stores low-rank neural network model which is pre-learned so as to differentiate normal cells from dangerous cells. The neural network mode may be configured in manufacturing process or may be downloaded from the neural network learning server 200. Further, the neural network model is a dedicated program which has lesion cell detecting algorithm for inspecting whether desquamated cells taken from patients are lesion cells or not.

Step (S120): While the low-rank neural network model is activated, the cell diagnosis device 100 is provided from outside with photos of desquamated cells which are taken from patients, i.e., inspection-subject cell photos. The procedure of taking inspection-subject cells from patients and then obtaining the inspection-subject cell photos may be carried out as a workflow. However, because this procedure is not crucial to the present invention, its detailed description shall be omitted herein.

Then, cell image processor 120 of the cell diagnosis device 100 provides the inspection-subject cell photos into the low-rank neural network model, e.g., in pixel basis.

Step (S130): Then, low-rank neural network model which is installed in the cell diagnosis device 100 executes a neural network data processing as shown in FIG. 6 as to the provided inspection-subject cell photos. As the low-rank neural network model outputs diagnostic result data, cell abnormality diagnoser 130 of the cell diagnosis device 100 detects whether the inspection-subject cell photos are of normal cells (i.e., 'no problem' or 'okay') or of dangerous cells (i.e., 'suspicious').

Step (S140): Meanwhile, lesion database 210 of the neural network learning server 200 stores sufficiently many pluralities of normal cell photos and lesion cell photos which are pre-classified by each kind of lesions. These are prepared so as to upgrade by DNN learning the low-rank neural network model which the cell diagnosis device 100 is utilizing in cell diagnosis.

Step (S150, S160): Then, NN model generator 220 of the neural network learning server 200 obtains high-rank neural network model which is more upgraded than current state through DNN learning procedure which the DNN learning processor 230 performs on the basis of the data of pluralities of normal cell photos and lesion cell photos of the lesion database 210.

Then, learning model provider 240 of the neural network learning server 200 provides the high-rank neural network model to the NN model updater 140 of the cell diagnosis device 100 by downloading via Internet. It is preferable that the download may be periodically performed.

Step (S170): Then, the NN model updater 140 of the cell diagnosis device 100 downloads the high-rank neural network model in more upgraded state from the neural network learning server 200 via Internet, and then upgrades the low-rank neural network model which is currently installed in the cell diagnosis device 100.

Step (S180): Meanwhile, it is preferable that data in the lesion database 210 of the normal cell photos and the lesion cell photos may be constantly updated. Because of this, by use of data which are obtained in the actual diagnosis process in hospitals, the neural network model of the cell diagnosis device 100 may be constantly upgraded.

Figure 8:
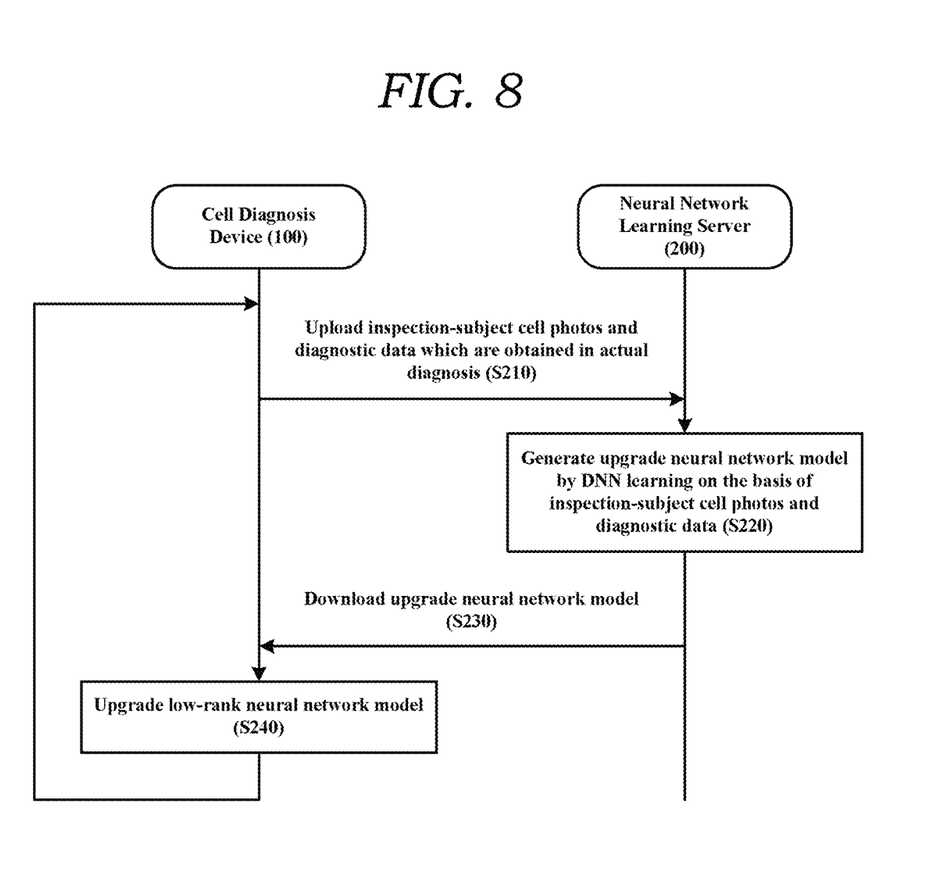
FIG. 8 is a flowchart illustrating another embodiment of cell abnormality diagnosis procedure using DNN learning according to the present invention.

FIG. 8 is a flowchart illustrating another embodiment of cell abnormality diagnosis procedure using DNN learning according to the present invention.

Step (S210): Meanwhile, the cell diagnosis device 100 obtains inspection-subject cell photos and diagnostic result data by results of actual diagnosis of patients using the low-rank neural network model, and then stores the same in a diagnosis database (not shown). Further, the diagnosis data provider 150 of the cell diagnosis device 100 obtains the inspection-subject cell photos and the diagnostic result data from the diagnosis database (not shown), and then uploads the same to the cumulative learning model generator 250 of the neural network learning server 200. It is preferable that the upload may be periodically performed.

Step (S220): Then, the cumulative learning model generator 250 of the neural network learning server 200 performs DNN learning on the high-rank neural network model on the basis of the inspection-subject cell photos and the diagnostic result data which has received from the cell diagnosis device 100 so as to generate an upgrade neural network model.

At this stage, the upgrade neural network model represents a neural network model which is specialized to the specific cell diagnosis device 100 having uploaded the inspection-subject cell photos and the diagnostic result data.

Step (S230): Then, the cumulative learning model provider 260 of the neural network learning server 200 provides the upgrade neural network model to the NN model cumulative updater 160 of the specific cell diagnosis device 100 by downloading, where the specific cell diagnosis device 100 is the one which has uploaded the inspection-subject cell photos and the diagnostic result data.

Step (S240): As a result, the NN model cumulative updater 160 of the cell diagnosis device 100 may upgrade the low-rank neural network model on the basis of the upgrade neural network model which is downloaded from the neural network learning server 200.

As described above, the cell diagnosis device 100 in each hospital uploads diagnostic result data of actual diagnosis result for patients to the neural network learning server 200, and the neural network learning server 200 generates upgrade neural network model by learning on the basis of the uploaded diagnostic result data and then provides the upgrade neural network model to the corresponding cell diagnosis device 100. By the procedure as above, the cell diagnosis device 100 in each hospital may provide the specialized diagnosis service.

Further, in FIGS. 7 and 8, the neural network learning server 200 is provided with cell lesion data for the DNN learning of neural network model. The cell lesion data may include digitalized information of error corrections which are done by reviewers (e.g., pathologists) as to a draft of diagnosis result by the cell diagnosis device 100. The cell diagnosis device 100 may generate errors by overlooking some parts in the inspection-subject cell photos or may generate errors of misdiagnosis.

The reviewers may mark on portions in slides corresponding to the errors with marker pens. Then, images of the marked portions may be provided to the neural network learning server 200 along with original inspection-subject cell photos and original diagnostic result data.

The cell lesion data shall be used in DNN learning on neural network by the neural network learning server 200, especially in enhancing one or more of pattern recognition algorithm and lesion feature searching algorithm.

Figure 9:
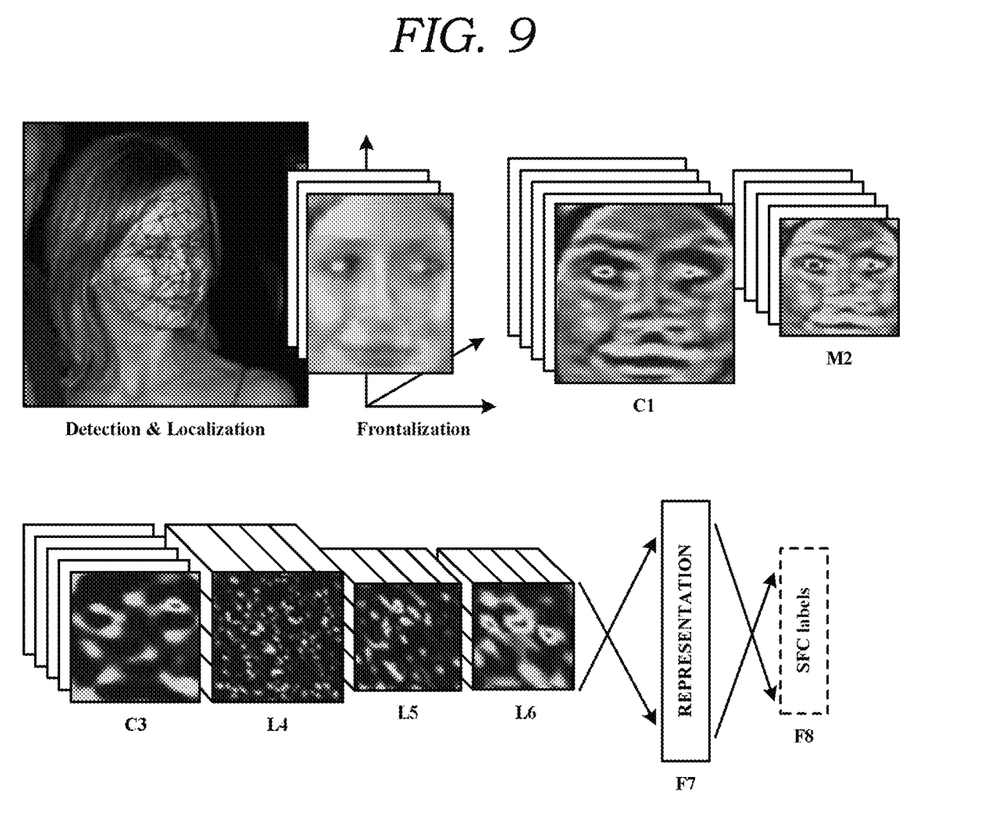
FIG. 9 is an exemplary view illustrating deep learning algorithm which is obtained by Internet search.
Figure 10:
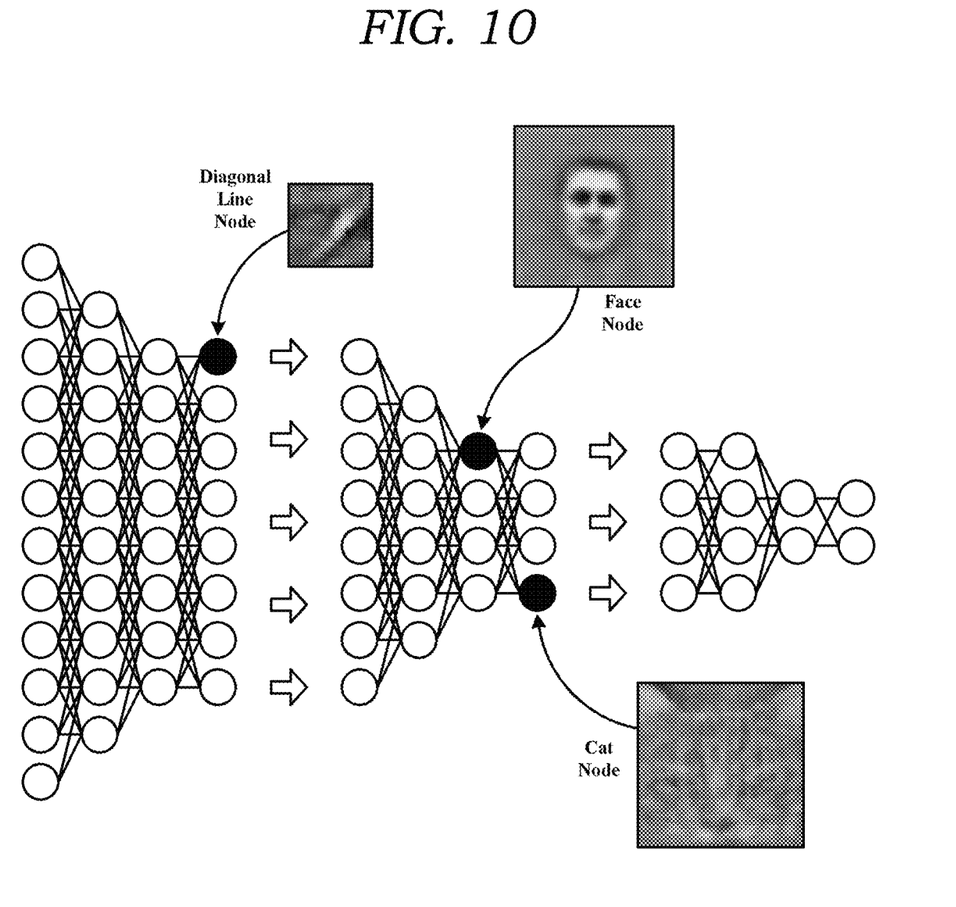
FIG. 10 is an exemplary view illustrating DNN learning algorithm obtained by Internet search.

FIG. 9 is an exemplary view illustrating deep learning algorithm which is obtained by Internet search in 'NAVER- CAST' website. FIG. 10 illustrates concept of DNN learning algorithm out of the deep learning algorithm which was applied into cat image recognition in 2012.

The "Deep Learning" technology refers to a technology by which computers may think and learn like a human, especially may group or categorize objects and data. For example, a computer after deep learning may differentiate dog photos from cat photos.

The "Machine Learning" has been proposed so as to make computers to identify objects like a human by deep learning. It is a technology by which computers, being provided with big volume of data, may categorize data by their similarity. For example, a computer which has been pre-learned with dog photos may identify new dog photos.

A lot of machine learning algorithms have been proposed on how computers may categorize learning data, for example, "Decision Tree", "Bayesian network", "Support Vector Machine (SVM)" and "Artificial neural network". The deep learning is a machine learning technique which is proposed for overcoming the limitation of "Artificial neural network" algorithm.

The Deep learning has two kinds of data categorization approach, i.e., supervised learning and unsupervised learning. In the supervised learning approach, a computer is trained with well-categorized information. However, in the unsupervised learning approach, a computer learns for itself without the training as above. In general, the unsupervised learning requires high computing performance.

DNN learning algorithm is one of the deep learning algorithms. There has been much research on the DNN learning technology, for example, voice search service of Jelly Bean which is Android OS of Google Inc., voice search service of Bing of Microsoft Corp., and voice recognition service of Naver Corp. of Korea.

In special, in 2012, Google implemented DNN learning by using 16,000 computer processors and 1 billions of neural networks, by which "cat" images were successfully recognized out of 10 millions of videos which were uploaded in YouTube. Following the unsupervised learning approach, the DNN-learned computers may recognize and categorize cat images for themselves without being taught on "how cat images are like".

In this regards, FIG. 10 shows an example of an application of DNN learning algorithm by YouTube. By the way, because the present invention does not claim to the DNN learning algorithm itself, the detailed description thereof shall be omitted herein.

The invention can also be embodied as computer readable codes on a non-transitory computer-readable medium. The non-transitory computer-readable medium is any data storage device that can store data which may be thereafter read by a computer system, e.g., CD-ROM, NAS, magnetic tape, had disk and web disk. Further, codes may be stored and executed in network-coupled storages in a distributed fashion.

The invention claimed is:

1. A cell abnormality diagnosis system using a Deep Neural Network learning comprising a cell diagnosis device installed in each hospital for determining normal cells or dangerous cells on the basis of a neural network as to inspection-subject cell photos and a neural network learning server being connected to a plurality of cell diagnosis devices via world-wide-web for performing the Deep Neural Network learning on the neural network for each of the cell diagnosis devices with a reflecting actual diagnosis result for patients in the corresponding hospital, wherein the cell abnormality diagnosis system comprising:

a cell diagnosis device installed in each hospital including:
a neural network modeler of storing a low-rank neural network model which is pre-learned so as to differentiate normal cells from dangerous cells,
a cell image processor of providing inspection-subject cell photos from outside into the low-rank neural network model in pixel basis,
a cell abnormality diagnoser of detecting abnormality out of the inspection-subject cell photos which is provided by the cell image processor,
a diagnosis data provider of uploading to the neural network learning server the inspection-subject cell photos and diagnostic result data which are obtained by the actual diagnosis result for patients in the hospital in which the cell diagnosis device is installed, and
a neural network model cumulative updater of downloading a upgrade neural network model being the Deep Neural Network learned from the neural network learning server so as to substitute the low-rank neural network model with the downloaded upgrade neural network model; and
the neural network learning server being connected to the plurality of cell diagnosis devices via world-wide-web for performing the Deep Neural Network learning on the neural network for each of the cell diagnosis device with reflecting actual diagnosis result for patients in corresponding hospital including:
a cumulative learning model generator of being uploaded by the cell diagnosis device with the inspection-subject cell photos and the diagnostic result data which are obtained by the actual diagnosis result for patients in the corresponding hospitals and then of performing the Deep Neural Network learning on the low-rank neural network model of the cell diagnosis device on the basis of the uploaded so as to generate an upgrade neural network model for the cell diagnosis device, and
a cumulative learning model provider, which is not the diagnosis data provider, of providing the upgrade neural network model by downloading to the cell diagnosis device which has uploaded the inspection-subject cell photos and the diagnostic result data.

2. The cell abnormality diagnosis system using the Deep Neural Network learning according to claim 1,
wherein the cell diagnosis device further comprising:
a neural network model updater, which is not the neural network model cumulative updater, upgrading the low-rank neural network model by downloading a high-rank neural network model from the neural network learning server via world-wide-web, and
wherein the neural network learning server further comprising:
a lesion database of storing pluralities of normal cell photos and lesion cell photos which are pre-classified by each kind of lesions,
a neural network model generator, which is not the cumulative learning model generator, of generating the high-rank neural network model on the basis of the normal or dangerous pre-classified data in the lesion database,
a Deep Neural Network learning processor of performing the Deep Neural Network learning for the high-rank neural network model on the basis of the normal or dangerous pre-classified data in the lesion database, and
a learning model provider, which is not the diagnosis data provider and not the cumulative learning model generator, of providing the high-rank neural network model to the NN model updater by downloading.

3. The cell abnormality diagnosis system using the Deep Neural Network learning according to claim 1,
wherein the cell diagnosis device 100 further comprising:
a low-rank model provider, which is not the diagnosis data provider and not the cumulative learning model generator and not the learning model provider, of uploading its own low-rank neural network model to the neural network learning server for the Deep Neural Network learning, and
wherein the cumulative learning model generator of the neural network learning server performs the Deep Neural Network learning on the low-rank neural network model which is provided by the low-rank model provider of the cell diagnosis device.

4. The cell abnormality diagnosis system using the Deep Neural Network learning according to claim 2, wherein the neural network learning server further comprising:
a low-rank model identifier of managing the recently downloaded neural network model for each of the cell diagnosis devices so as to identify the low-rank neural network model of the cell diagnosis device which has uploaded the inspection-subject cell photos and the diagnostic result data and so as to provide the identified low-rank neural network model to the cumulative learning model generator.

5. The cell abnormality diagnosis system using the Deep Neural Network learning according to claim 1,
wherein the cell diagnosis device further comprising:
a diagnosis database of collecting inspection-subject cell photos and diagnostic result data by actual diagnosis of patients.

* * * * *